(12) United States Patent
Krishnamoorthy et al.

(10) Patent No.: US 9,878,090 B2
(45) Date of Patent: Jan. 30, 2018

(54) MINIATURIZED ELECTROTHERMAL FLOW INDUCED INFUSION PUMP

(71) Applicant: CFD Research Corporation, Huntsville, AL (US)

(72) Inventors: Sivaramakrishnan Krishnamoorthy, Madison, AL (US); Guiren Wang, Huntsville, AL (US); Jianjun Feng, Cincinnati, OH (US); Yi Wang, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 238 days.

(21) Appl. No.: 14/971,715

(22) Filed: Dec. 16, 2015

(65) Prior Publication Data

US 2016/0235912 A1 Aug. 18, 2016

Related U.S. Application Data

(62) Division of application No. 11/516,269, filed on Sep. 6, 2006, now Pat. No. 9,283,597.

(51) Int. Cl.
*A61M 5/142* (2006.01)
*B01F 13/00* (2006.01)
(Continued)

(52) U.S. Cl.
CPC ..... *A61M 5/14244* (2013.01); *B01F 13/0079* (2013.01); *B01F 13/0081* (2013.01);
(Continued)

(58) Field of Classification Search
CPC ........ B01L 3/5027; B03C 5/026; B03C 5/005
See application file for complete search history.

(56) References Cited

U.S. PATENT DOCUMENTS 2,570,158 A * 10/1951 Schissel ................. H01J 49/38
250/282
4,001,102 A * 1/1977 Batha .................... B01D 57/02
204/547

(Continued)

OTHER PUBLICATIONS

Perch-Nielsen et al., Numerical Simulation of Travelling Wave Induced Electrothermal Fluid Flow, Jul. 28, 2004, Journal of PhysicisD: Applied Physics 37 (2004) 2323-2330.

(Continued)

*Primary Examiner* — Imani Hayman
*Assistant Examiner* — Matthew A Engel
(74) *Attorney, Agent, or Firm* — Maschoff Brennan

(57) ABSTRACT

A micropump that pumps liquid using electrothermally-induced flow is described, along with a corresponding self-regulating pump and infusion pump. The micropump has applications in microfluidic systems, such as biochips. The self-regulating infusion pump is useful for administration of large and small volumes of liquids such as drugs to patients and can be designed for a wide range of flow rates by combining multiple micropumps in one infusion pump system. The micropump uses electrode sequences on opposing surfaces of a flow chamber that are staggered with respect to each other. The opposing surfaces include staggered electrodes that have the same phase and same electrode sequence. As such electrodes with the same phase are staggered and not eclipsed.

20 Claims, 11 Drawing Sheets

(51) Int. Cl.

| | | |
|---|---|---|
| *B01L 3/00* | (2006.01) | |
| *B01L 99/00* | (2010.01) | |
| *B08B 7/00* | (2006.01) | |
| *B08B 9/00* | (2006.01) | |
| *F04B 19/00* | (2006.01) | |
| *F04B 19/24* | (2006.01) | |
| *G01N 30/00* | (2006.01) | |

(52) U.S. Cl.
CPC ............ *B01L 99/00* (2013.01); *B08B 7/0064* (2013.01); *B08B 9/00* (2013.01); *F04B 19/006* (2013.01); *F04B 19/24* (2013.01); *A61M 2205/0244* (2013.01); *B01L 3/5027* (2013.01); *B01L 2300/1833* (2013.01); *B01L 2400/0415* (2013.01); *B01L 2400/0442* (2013.01); *B01L 2400/0493* (2013.01); *B01L 2400/0496* (2013.01); *G01N 2030/0035* (2013.01); *G01N 2030/0065* (2013.01)

(56) References Cited

U.S. PATENT DOCUMENTS

| | | | | |
|---|---|---|---|---|
| 4,390,403 | A * | 6/1983 | Batchelder | B03C 5/022 |
| | | | | 204/547 |
| 4,418,346 | A * | 11/1983 | Batchelder | G09F 9/372 |
| | | | | 345/107 |
| 4,443,218 | A * | 4/1984 | DeCant, Jr. | A61M 5/14276 |
| | | | | 128/DIG. 12 |
| 5,626,734 | A * | 5/1997 | Docoslis | B03C 5/026 |
| | | | | 204/547 |
| 5,795,457 | A * | 8/1998 | Pethig | B03C 5/026 |
| | | | | 204/547 |
| 5,888,370 | A * | 3/1999 | Becker | B03C 5/028 |
| | | | | 204/547 |
| 5,993,630 | A * | 11/1999 | Becker | B03C 5/028 |
| | | | | 204/547 |
| 5,993,632 | A | 11/1999 | Becker | |
| 6,149,789 | A * | 11/2000 | Benecke | B01F 13/0076 |
| | | | | 204/547 |
| 6,352,838 | B1 * | 3/2002 | Krulevitch | C12N 15/101 |
| | | | | 204/547 |
| 6,748,266 | B2 * | 6/2004 | Bernabei | A61H 7/008 |
| | | | | 604/20 |
| 7,010,343 | B2 * | 3/2006 | Bernabei | A61H 7/008 |
| | | | | 601/117 |
| 7,105,081 | B2 * | 9/2006 | Gascoyne | B03C 5/005 |
| | | | | 204/547 |
| 7,520,875 | B2 * | 4/2009 | Bernabei | A61H 7/008 |
| | | | | 604/20 |
| 7,998,328 | B2 * | 8/2011 | Feng | B03C 5/005 |
| | | | | 204/450 |
| 9,283,597 | B2 * | 3/2016 | Krishnamoorthy | |
| | | | | A61M 5/14244 |
| 2002/0036141 | A1 * | 3/2002 | Gascoyne | B03C 1/00 |
| | | | | 204/547 |
| 2004/0011650 | A1 * | 1/2004 | Zenhausern | B01L 3/502746 |
| | | | | 204/547 |
| 2004/0011651 | A1 * | 1/2004 | Becker | B03C 5/026 |
| | | | | 204/547 |
| 2004/0015190 | A1 * | 1/2004 | Bernabei | A61H 7/008 |
| | | | | 607/3 |
| 2004/0097900 | A1 | 5/2004 | Keren et al. | |
| 2004/0220622 | A1 * | 11/2004 | Bernabei | A61H 7/008 |
| | | | | 607/3 |
| 2005/0014129 | A1 * | 1/2005 | Cliffel | G01N 33/5005 |
| | | | | 435/4 |
| 2005/0101901 | A1 * | 5/2005 | Gura | A61M 1/16 |
| | | | | 604/5.02 |
| 2005/0148064 | A1 * | 7/2005 | Yamakawa | B01L 3/502753 |
| | | | | 435/287.2 |
| 2007/0020124 | A1 | 1/2007 | Singhal et al. | |
| 2007/0110625 | A1 * | 5/2007 | Krishnamoorthy | |
| | | | | A61M 5/14244 |
| | | | | 422/400 |
| 2010/0012496 | A1 * | 1/2010 | Tsunazawa | B03C 5/005 |
| | | | | 204/547 |
| 2011/0020141 | A1 * | 1/2011 | Van Zon | B01L 3/50273 |
| | | | | 417/50 |

OTHER PUBLICATIONS

Collins, John; Lee, Abraham P. (2004) "Microfluidic Flow Transducer Based on the Measurement of Electrical Admittance" Lab Chip 4:7-10.

Yao, S. et al. (2003) Porous Glass Electroosmotic Pumps: Design and Experiments: J. Colloid and Interface Sci/ 268:143-153.

Wang, J. R. (2005) "Laser Induced Fluorescence Photobleaching Anemometer for Microfluidic Devices" Lab Chip 5:450-456.

Wang, J. R., et al. (2004) "A Laser Induced Cavitation Pump" J. Micromech, Microeng. 14:1037-1046.

Laser D. J. and Santiago, J. G. (2004) "A Review of Micropumps" J. Micromech. Microeng. 14:R35-R64.

* cited by examiner $Q_{max} = 0.065$ mL/min
$P_{max} = 0.32$ mmHg $Q_{max} = 0.078$ mL/min
$P_{max} = 0.383$ mmHg

MINIATURIZED ELECTROTHERMAL FLOW INDUCED INFUSION PUMP

CROSS-REFERENCE TO RELATED APPLICATIONS

This patent application is a divisional application of U.S. Ser. No. 11/516,269 filed Sep. 6, 2006, which application is incorporated herein by specific reference in its entirety.

STATEMENT REGARDING FEDERALLY SPONSORED RESEARCH OR DEVELOPMENT

The U.S. Government may have certain rights in this invention pursuant to SBIR Contract Number: W81WHO6C0067 awarded by the United States Army

INCORPORATED-BY-REFERENCE OF MATERIAL SUBMITTED ON A COMPACT DISC

Not Applicable

BACKGROUND OF THE INVENTION

Field of the Invention

The invention is a self-regulated Electrothermal Flow (ETF) micropump for infusion of fluids into the body of a patient. The self-regulated ETF micropump can also be used other application requiring miniaturized, self-regulating pumps. The micropump monitors flow rates using Laser-Induced Fluorescence Photobleaching Anemometry (LIFPA), impedance anemometry, or other flow measuring device. Data from fluid monitoring is transferred to a control system that controls the flow rate generated by the pump. The operation of the micropump can be set to maintain a constant flow rate or to deliver a pre-programmed flow rate pattern, for example.

Description of Related Art

Infusion pumps have a wide range of applications such as the controlled delivery of antibiotics, antiviral agents, anesthesia, chemotherapy, total parenteral nutrition (TPN), and patient-controlled analgesia. Control of infusion rates is particularly important for delivering small volumes of high concentration drugs and high flow rate infusions of large volumes.

Miniaturized, self-regulated flow pumps for drug infusion allow, for example, the controlled delivery of concentrated drug over extended periods to ambulatory patients (low flow rate) and the controlled infusion of high volumes of fluids (high flow rate).

Miniaturized electrokinetic pumps to move fluids through microfluidic devices are known and employ a variety of elecrtokinetic phenomena including electroosmotic flow, and electrohydrodynamic flow. Electokinetic pumps and their advantages are described in Fuhr G et al. (1994) J. Micromech. Microeng. 4:217-226; Laser D J and Santiago J G (2004) J. Micromech. Microeng. 14:R35-R64; Wang, G R et al. (2004) J. Micromech. Microeng. 14:1037-1046; Yao S et al. (2001) Proc. 2001 ASME Int. Mechanical Engineering Congress and Exposition; Yao S H et al. (2003) J. Colloid Interface Sci. 268:143-53; and Corbin et al. US 2005/0084385 A1, which are incorporated by reference in their entirety.

The use of time varying waveform ETF, such as traveling-wave ETF in applications such as micropumps is disclosed in U.S. Ser. No. 10/307,907, filed 2 Dec. 2002, which is incorporated by reference in its entirety. Unlike other electrokinetic phenomena, the ETF generated by the present invention provides mean pumping velocities that increase with the 4th power of the applied voltage. This enables ETF pumps to generate higher flow rates and hence, head pressures than existing electrokinetic pumps. A theoretical description of ETF is described in Ivan R et al. (2004) J. Phys. D: Appl. Phys. 37:2323-2330, which is incorporated by reference in its entirety.

In addition to providing high flow rates and/or head pressures through the use of ETF, the present invention provides for a self-regulating micropump that monitors the pump's flow rate. This is accomplished by coupling a flow rate monitor or sensor with a pump power supply controller. The flow rate produced by the pump is measured using, for example, Laser-Induced Fluorescence Photobleaching Anemometry (LIFPA) or Flow Induced Differential Electrochemical Impedance Spectroscopy (FI-DEIS). These methods are described in Wang G R and Fiedler H E (2000) Experiments in Fluids 265-274; Wang G R (2005) Lab on a Chip. 5:450-456; Fiedler, H. E.; Wang, G. R. (1998) Deutsches Patent. No. 19838344.4; and Collins J and Lee A P (2004) Lab. Chip. 4:7-10, which are incorporated by reference in their entirety.

BRIEF SUMMARY OF THE INVENTION

The present invention involves drug infusion apparatus and methods comprising an ETF micropump, an anemometer, and a micropump controller in communication with both the micropump and anemometer. Self-regulation of flow rates is exemplified using LIFPA and FI-DEIS for flow rate sensing. The applications of the present invention include drug delivery by infusion and auto-controlled pumping in microfluidic systems and biochips.

DETAILED DESCRIPTION OF THE INVENTION

Figure 1A:
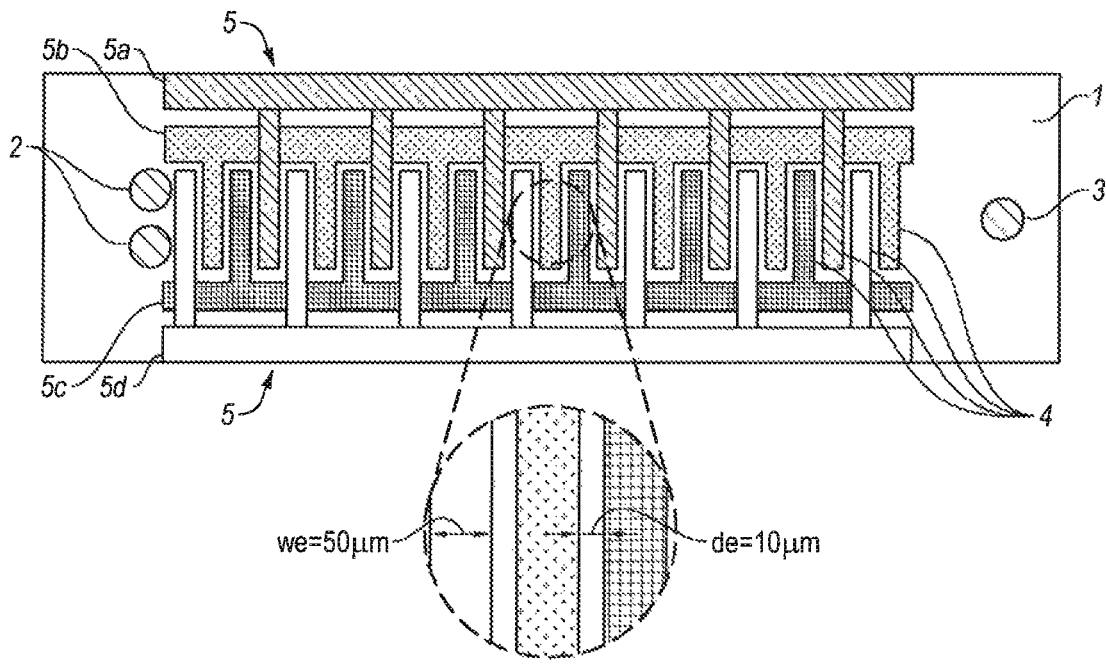
FIGS. 1A and 1B show a top view (FIG. 1A) and a side view (FIG. 1B) of an ETF micropump with opposed, aligned sets of parallel electrodes.

In one aspect, the present invention is a method for automatically controlling the flow of an ETF pump using an inline flow sensor and power supply controller. In another aspect, the invention is an apparatus for delivering drugs by infusion comprising a self-regulated EFT flow pump. In yet another aspect, the invention is a method for delivering drugs by infusion using a self-regulated EFT flow pump.

The ETF micropump minimally comprises a pumping chamber containing a fluid to be pumped, an inlet into and an outlet from the pumping chamber, at least one set of four elongated electrodes arranged in parallel in one wall of the pumping chamber in contact with the fluid, and a power supply electrically coupled to each of the electrodes in such a way as to produce a traveling wave ETF (tw-ETF) of fluid within the volume of the pumping chamber in a direction perpendicular to the elongated electrodes. The pumping chamber may have multiple sets of 3 or, preferably, 4 or more parallel electrodes located in one or opposing walls of the chamber. These electrodes are activated in a phase-shifted manner to produce ETF of the fluid to be pumped with a phase shift of 2irin for n electrodes per set.

The efficiency increases with the number of phase-shifted electrodes in a set. There is practical limit to the number of phase-shifted electrodes in a set, however, because the number of electrical leads required is equal to the number of electrodes in a set. Phase-shifted electrode sets may optimally be located on opposing walls directly across from one another (eclipsed), or offset in the direction normal to the electrodes by an offset distance (staggered). Additionally, electrodes within a set may be located on opposing walls in a staggered configuration. Each of the preceding configurations is described in more detail in the examples. The numbers and locations of electrodes in a set, sets of electrodes, inlets and outlets, and channel dimensions are variable and may be changed to suit particular applications needs.

The flow channel is optimally made of a material that is electrically insulating such as glass, silicon, PDMS, or other plastic. Electrodes are optimally made of gold or other electrically conducting material that does not react chemically with the fluid being pumped.

Computational simulations validated using experimental results conducted by the inventors indicate that the head pressure generated by the ETF pump increases linearly with the length of the pumping chamber and that reducing the gap between electrodes and increasing the number of electrodes improves the performance of the pump. Further improvements in flow rate can be achieved by stacking pumping chambers within a single micropump.

Guidance for Micropump Design:

Optimal performance can be achieved by a simulation-based design approach based on the following description. When an electric current is passed through a conducting fluid, it induces Joule heating and creates a temperature gradient. The electrical properties such as permittivity and conductivity vary with temperature and thereby with the spatial location. Under the action of externally imposed electric field, this non-uniformity in the dielectric property of the liquid induces dielectric forces leading to bulk fluid flow known as electrothermal induced flow. The flow rate and the associated maximum pressure head depend on electrode dimension, form, electrode distance and configuration, channel dimensions, applied voltages, fluid properties and phase shifts in the electric field.

The steady state free charge density is described by $$\rho_e = \frac{1}{\tau} D \cdot \nabla \tau, \tau = \frac{\sigma}{\varepsilon} \tag{1}$$

where D is the electric displacement, σ and ∈ are conductivity and dielectric constant. The intrinsic electric relaxation time τ represents the time needed by a free charge to relax from the fluid to its external boundary and thus determines different responses to AC electric signal. The electrostatic force applied to dielectric material is given by $$\bar{f} = \rho_q \bar{E} - \frac{1}{2} E^2 \nabla \varepsilon + \frac{1}{2} \nabla \left[ \rho_m \left( \frac{\partial \varepsilon}{\partial \rho_m} \right)_T E^2 \right] \tag{2}$$

Here $p_m$ is the fluid density and $\bar{E}$ is electric field. For most experimental conditions of practical interest in which harmonically oscillating AC field is applied to produce non-uniform electric field, the averaged force density is approximately given by $$\langle \bar{f} \rangle = \frac{1}{2} \text{Re} \left[ \frac{\sigma \varepsilon (\alpha - \beta)}{\sigma + i\omega\varepsilon} (\nabla T \cdot \bar{E}_0) \bar{E}_0^* \right] - \frac{1}{2} \varepsilon \alpha |\bar{E}_0|^2 \nabla T \tag{3}$$

where $$\alpha = \frac{1}{\varepsilon} \frac{\partial \varepsilon}{\partial T}, \beta = \frac{1}{\sigma} \frac{\partial \sigma}{\partial T} \tag{4}$$

ω is the angular frequency of the AC signal, $i=\sqrt{-1}$, and T is the temperature. The superscript star represents for complex conjugate. Joule heating due to electric current is the primary heat resource and is related to the current by $$j = \sigma E^2 \tag{5}$$

When this intrinsic time scale is comparable to period of AC signal, the force density exhibits traveling wave features that respond to phase shift in the applied field. At small amplitudes, the flow and thermal fields can be linearized and the scaling analysis indicates that the velocity and temperature vary as V4 and V2, respectively, where V is externally applied voltage. Detailed scaling analysis of linearized governing equations indicate that the average velocity induced can be expressed as:

$$U_0 \propto \frac{\sigma V^4}{\mu k L_0} \tag{6}$$

The scaling of flow rate is $\sigma V^4 L_0/(\mu k)$. In general, the flow rate increases with increasing applied potential, increasing solution conductivity, and/or increasing channel size.

Example 1

Etf Micropump with Opposed, Aligned Sets of Electrodes

Figure 1B:
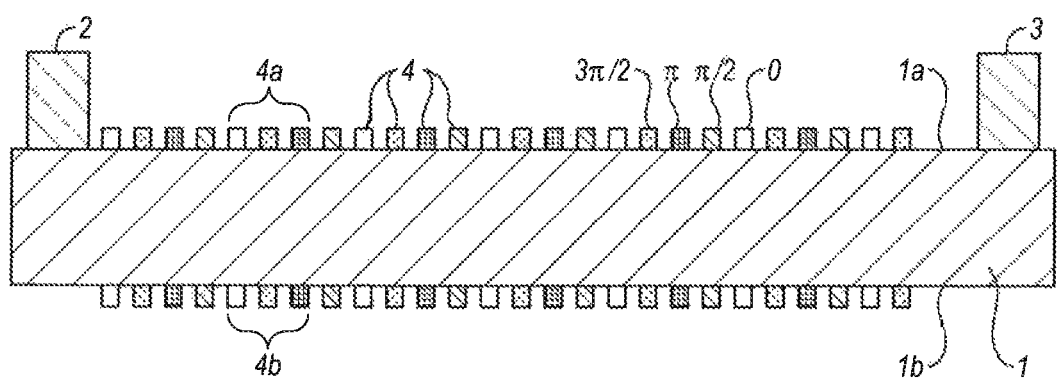

A first exemplary embodiment of an ETF micropump having opposed sets of parallel electrodes on the top and bottom surfaces of a flow chamber is shown in FIGS. 1A and 1B. The figure shows a flow chamber 1, two inlets 2, one outlet 3, electrodes 4, and electrical leads 5, four each for the electrodes in the top wall 1a and bottom wall 1b surfaces. Four electrical leads (e.g., electrical leads 5a, 5b, 5c, and 5d are shown as top electrical leads 5, where the bottom electrical leads 5 are not shown because they are eclipsed by the top electrical leads 5) are required for each of the top and bottom channels so that properly time delayed electric waveform fields can be applied. The figure illustrates only 52 total electrodes to clearly show the principle of the design. The actual design comprises 216 electrodes. An AC signal is applied to the electrode array with the phase shifted by $\pi/2$ between adjacent pairs. The markings on electrodes 4 in FIGS. 1A and 1B indicate the pattern of phase shifting. The flow chamber is 10 mm wide, 20 mm long, and 170 µm deep and the electrodes are 50 µm wide, 1 cm long, and are spaced 10 µm apart. The shading indicates which electrodes are coupled to the same leads. The electrodes in the bottom surface of the flow chamber are eclipsed by the electrodes in the top surface in the top view. The electrical leads are not shown in the side view and are insulated from one another. This prototype produces a theoretical flow rate of 1.8 mL/min and a head pressure of 1.4 mmHg. As shown, there is a first electrode set 4a of three sequentially arranged parallel elongate electrodes in the top wall 1a, and a second electrode set 4b of three sequentially arranged parallel elongate electrodes in the bottom wall 1b.

Example 2

Tw-ETF Micropump with Sets of Opposed, Staggered Electrodes

Figure 2A:
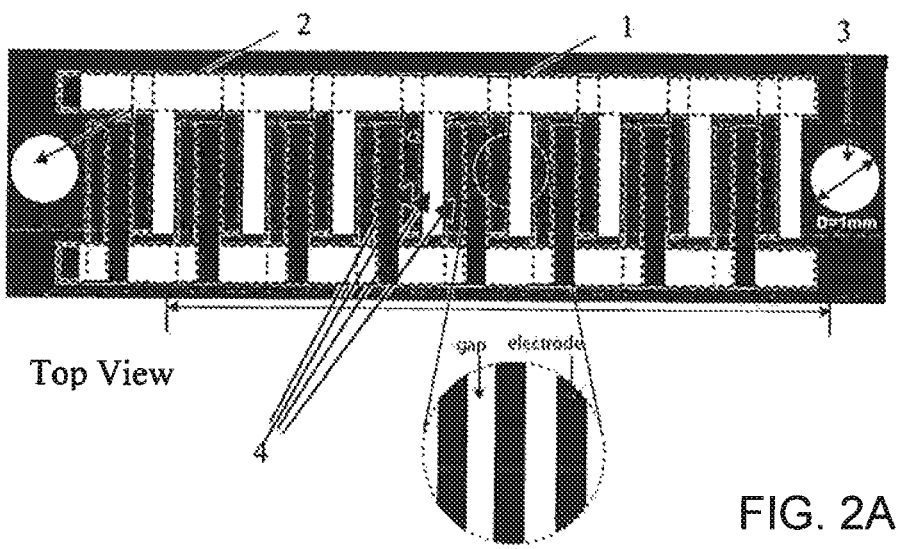
FIGS. 2A and 2B show top (FIG. 2A) and side (FIG. 2B) views of an ETF micropump with opposed, staggered sets of parallel electrodes.
Figure 2B:
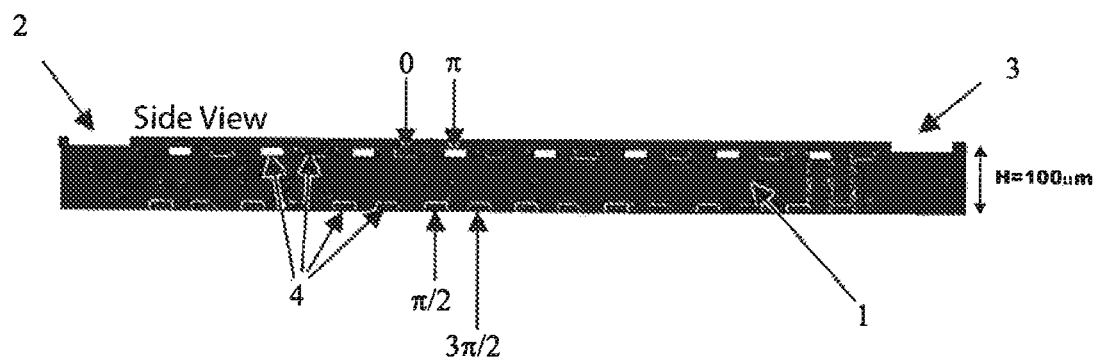

FIGS. 2A and 2B illustrate one example of an ETF micropump with opposed electrodes that are staggered, rather than aligned. The top and bottom electrodes are staggered by one electrode width to induce unidirectional ETF. In this embodiment, there are only two leads 5 each to the top and bottom of the pump because the repeating set of 4 electrodes is split between opposing sides. This configuration is less efficient than that shown in FIGS. 1A and 1B, but reduces the total number of leads required, making this embodiment easier to manufacture. The pumping chamber 1 is 10 mm wide, 15 mm long, and 100 µm deep and the electrodes 4 are 50 µm wide, 10 mm long, and are spaced 50 µm apart. The electrodes of the bottom surface are shown in FIG. 2A as dashed lines to show their positions relative to the electrodes in the top surface. The figure illustrates only 32 total electrodes to clearly explain the design. The actual design and fabricated micropump 5 comprise 128 electrodes.

Example 3

Manufactured Etf Micropump

Figure 3:
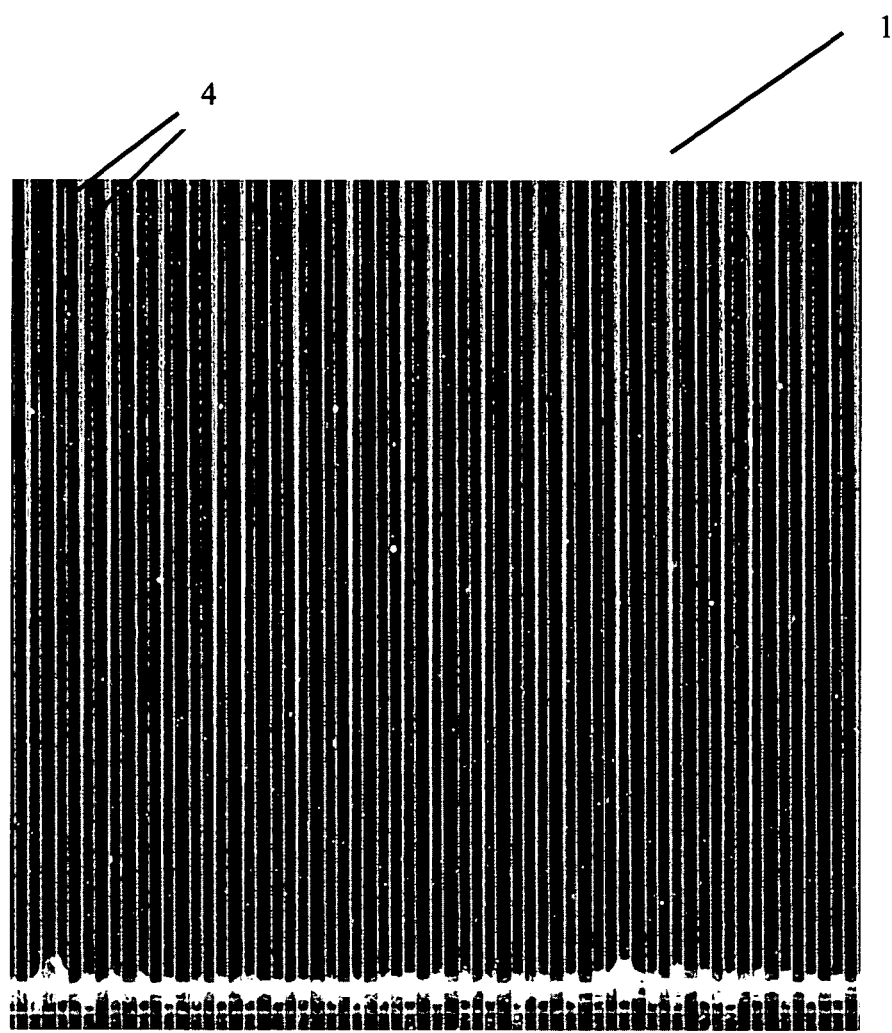
FIG. 3 shows a portion of a manufactures ETF micropump.
Figures 4A, 4B:
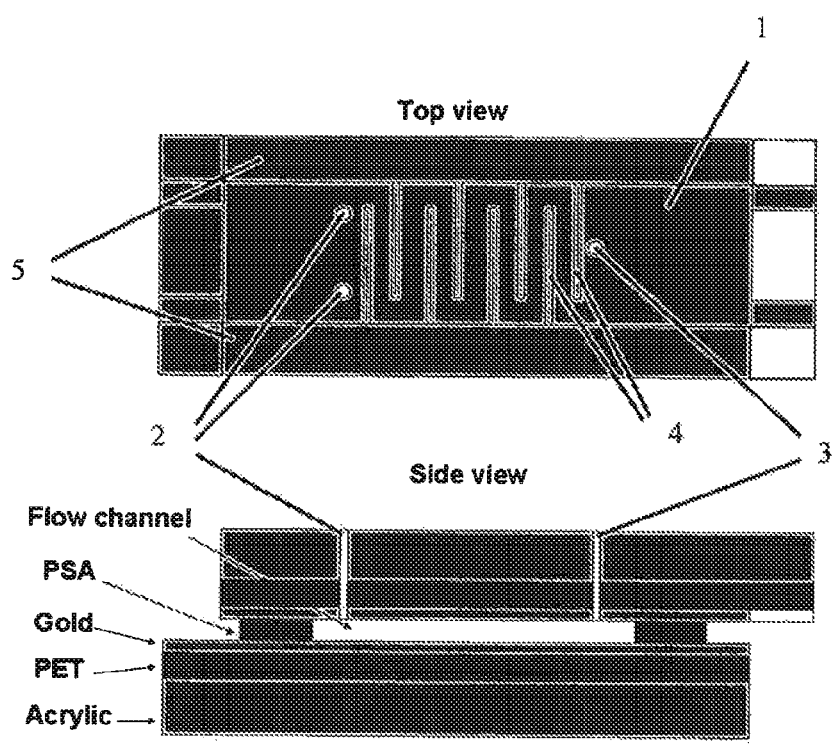
FIGS. 4A and 4B show the locations of fabrication components from the top (FIG. 4A) and side (FIG. 4B).

A portion of a ETF micropump manufactured according to the design in Example 2 and having transparent top and bottom walls is shown in FIG. 3. The pump was made using plastic-lamination technology comprising a polyester terphthalate (PET) sheet coated with gold. The integrated digital electrodes (IDEs) were obtained by laser etching of gold or ITO PET. The PET was glued to an acrylic sheet substrate. The pump was constructed by gluing different layers with pressure sensitive adhesives (PSA), which was also used to form the flow channel. Top and side views of illustrating the relative locations of fabrication components are shown in FIG. 4A and FIG. 4B. The micropump chip fabricated based on the design shown in FIGS. 2A and 2B, is 76 mm long, 45 mm wide and 3.8 mm high. The flow channel 1 is 40 mm long, 10 mm wide and 0.1 mm high. The length of flow channel covered with IDEs is 34.5 mm. The distance between the neighbor electrodes 4 on the bottom and top surfaces is 50 µm. All electrodes 4 have a width of 50 µm. Top and bottom electrodes are staggered by an electrode width. This micropump chip was used to measure flow rates by visually tracking particle movement in the pumping chamber.

Example 4

ETF Micropump Operation

Figure 5:
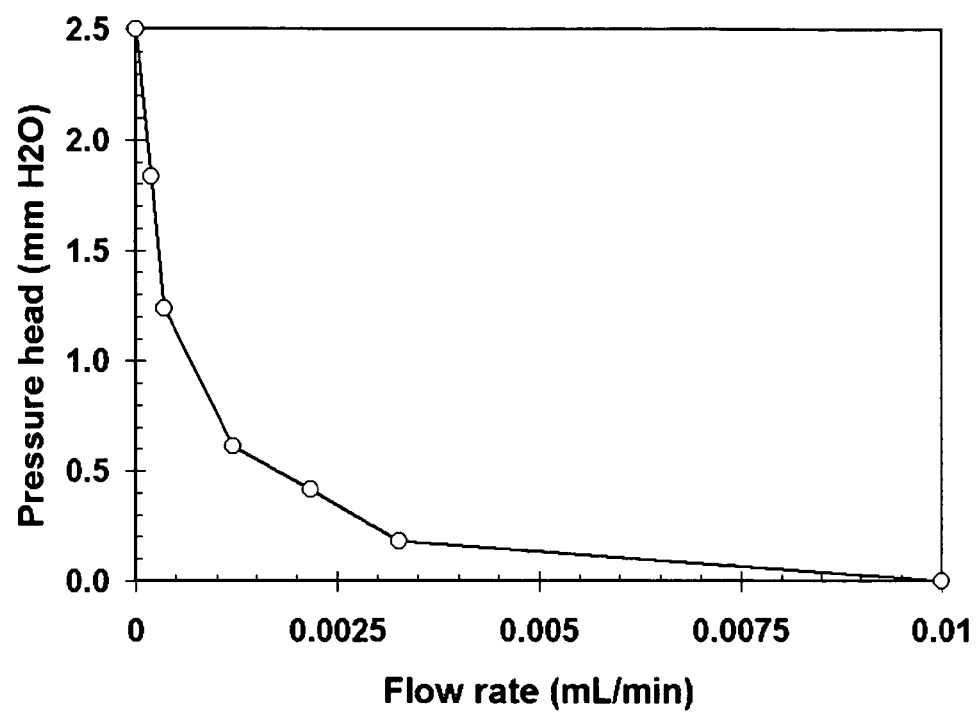
FIG. 5 shows a relationship between flow rate and pressure head for an embodiment of the invention

The flow generated by the pump in FIGS. 4A and 4B was visualized using fluorescent polystyrene microparticles of 1 µm in diameter. A phase shift of the AC signal to adjacent electrodes of 90° was used, with a frequency of 20 Vp-p and 500 kHz. The characteristic of the pump that shows the relationship between flow rate and pressure head is shown in FIG. 5. According to published theories of ETF, the relationship between head pressure and flow rate in linearly inverse. Experimental data from one prototype ETF pump unexpectedly shows that the relationship is more complex, affecting the optimal operating parameters for the pump. This micropump was used to pump a wide variety of aqueous buffer solutions, ethyl alcohol, and aqueous-alcohol solutions. The maximum flow velocity for a fluid increases with conductivity. Consequently, for liquids having low conductivities, the addition to the liquid of a buffer or other substance to increase 5 conductivity increases pumping efficiency significantly.

Figure 6:
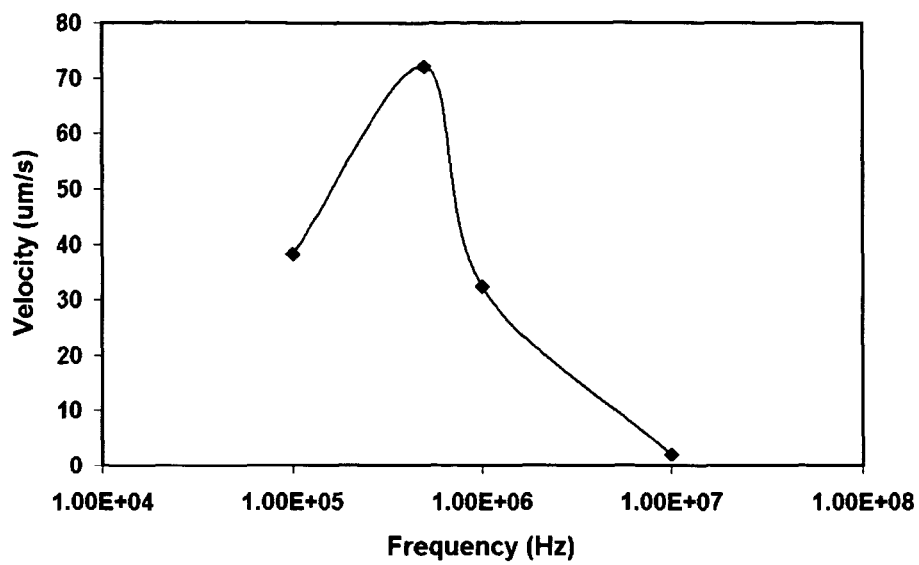
FIG. 6 shows a relationship between flow velocity and AC frequency for an embodiment of the invention.

Experimental data showing the relationship between flow velocity and AC frequency for an aqueous inositol solution in the micropump shown in FIGS. 4A and 4B are shown in FIG. 6. The frequency corresponding to maximum flow velocity is about 500 kHz. Additional experiments indicate that the critical frequency corresponding to the maximum flow velocity does not change with conductivity and basically stays in a frequency band of roughly 0.5-2 MHz for conductivities in the range of 1-1000 µS/cm.

Figure 7:
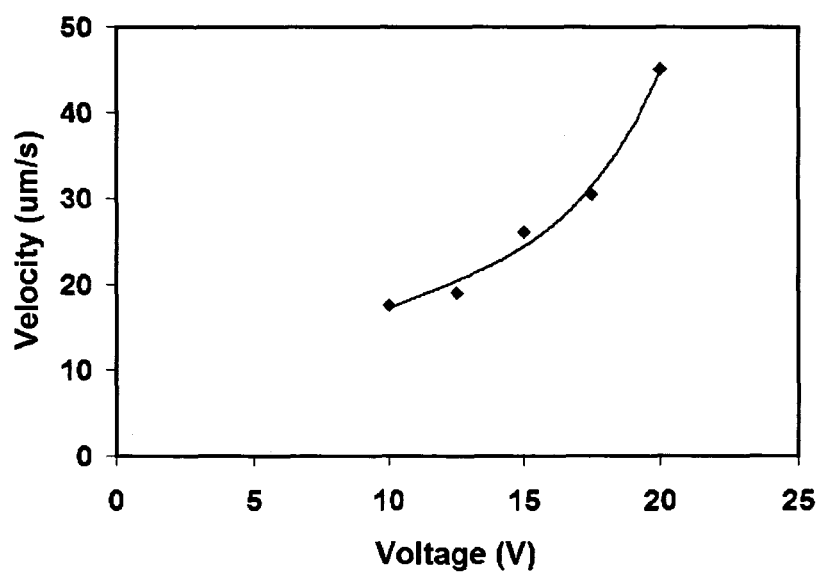
FIG. 7 is a graph showing the relationship between flow rate and applied voltage for an embodiment of the invention.

The magnitude of the electric field is controlled by the applied AC voltage. Theoretically, ETF velocity increases with the fourth power in voltage, as opposed to second power variation in electroosmotic flow. Experimental data demonstrating ETF in a fabricated micropump of the present invention is shown in FIG. 7. The flow rate can be dramatically increased by relatively mild increases in the voltage, providing the ability to achieve higher flow rates than electroosmotic flow driven micropumps. This is important because excessive increases in voltage can cause excessive heating that can inactivate drugs for infusion or generate bubbles in microfluidic systems.

Example 5

Additional Designs Having Eclipsed, Opposing Electrodes

Figure 8A:
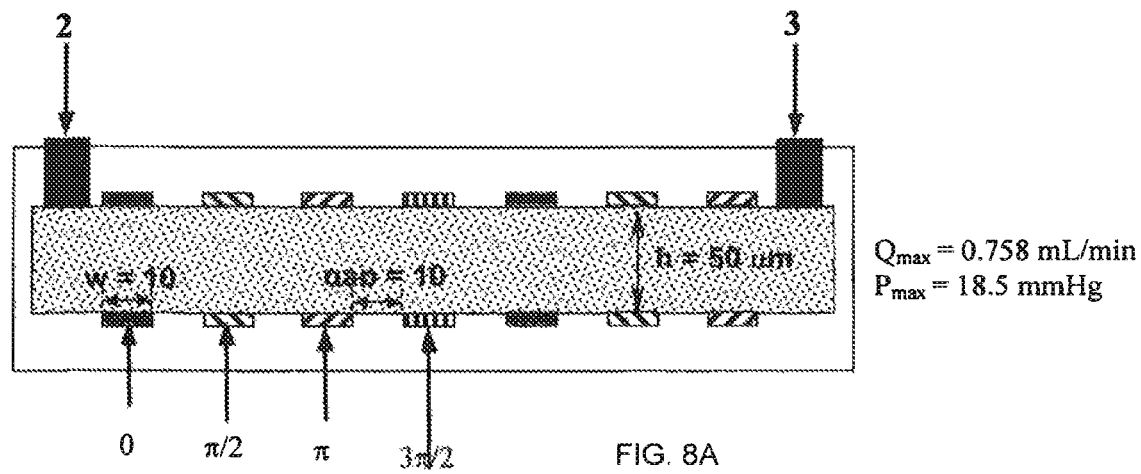
FIGS. 8A and 8B compare the theoretical maximum flow rates and head pressures for two embodiments of the invention having opposed, eclipsed electrodes.
Figure 8B:
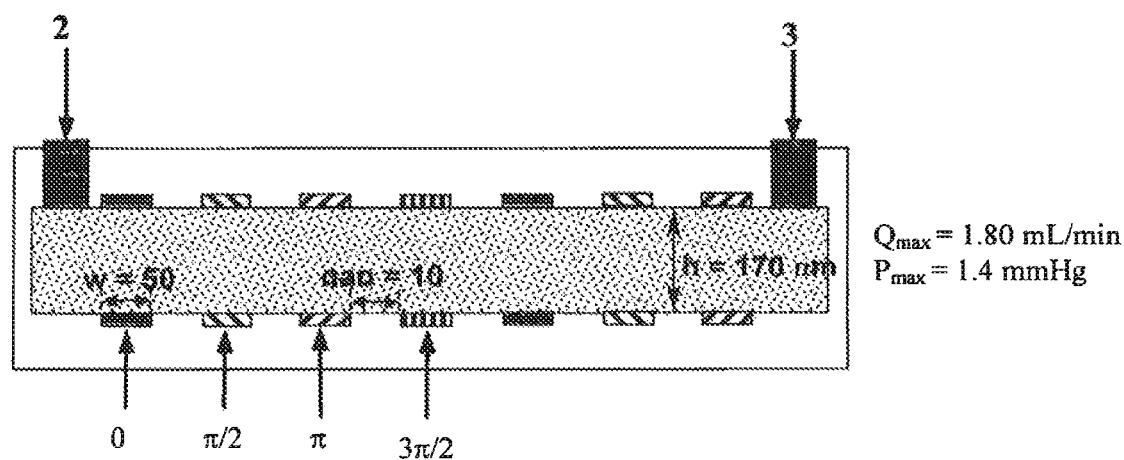

The effects of changing the width of electrodes on flow rate and head pressure of an eclipsed electrode design are shown in FIG. 8A and FIG. 8B. Both micropump designs have one inlet and one outlet, both 1 mm in diameter; 216 electrodes spaced 10 µm apart; and pumping chambers that are 2 cm long and 1 cm wide. The pumping chamber in FIG. 8A is 50 μm deep and the electrodes and the electrodes are 10 μm wide. The pumping chamber in FIG. 8B is 50 μm deep and the electrodes are 50 μm wide. Simulations of both designs were performed using CFD-ACE+® (ESI Group) and the maximum flow rates were calculated to be 0.758 mL/min for the first design and 1.8 mL/min for the second. Maximum head pressures were calculated to be 18.5 mmHg and 1.4 mmHg, respectively.

Example 6

Effects of Electrode Gap Distance on Staggered Designs

Figure 9A:
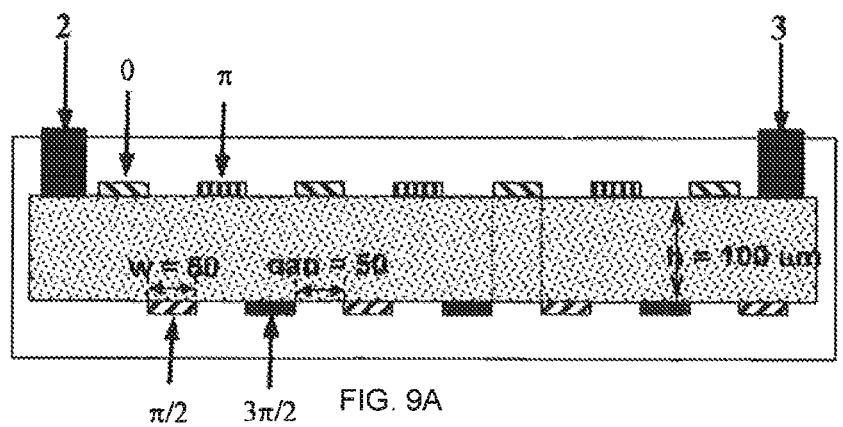
FIGS. 9A and 9B compare the theoretical maximum flow rates and head pressures for two embodiments of the invention having opposed, staggered electrodes.
Figure 9B:
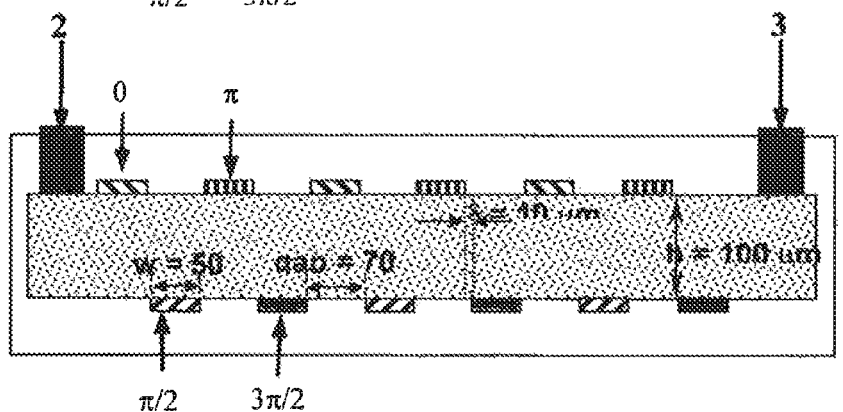

The effects of changing the width of gaps between electrodes on flow rate and head pressure of a staggered electrode design are shown FIG. 9A and FIG. 9B. Both micropump designs have one inlet and one outlet, both 1 mm in diameter; 216 electrodes that are 50 μm wide; and pumping chambers that are 4 cm long, 1 cm wide, and 100 μm deep. The gap between electrodes in FIG. 9A is 50 μm wide and the electrodes in FIG. 9B 70 μm wide. Simulations of both designs were performed as in the previous example and the maximum flow rates were calculated to be 0.065 mL/min for the first design and 0.078 mL/min for the second. Maximum head pressures were calculated to be 0.32 mmHg and 0.383 mmHg, respectively.

Example 7

Lifpa Flow Sensor

Figure 10:
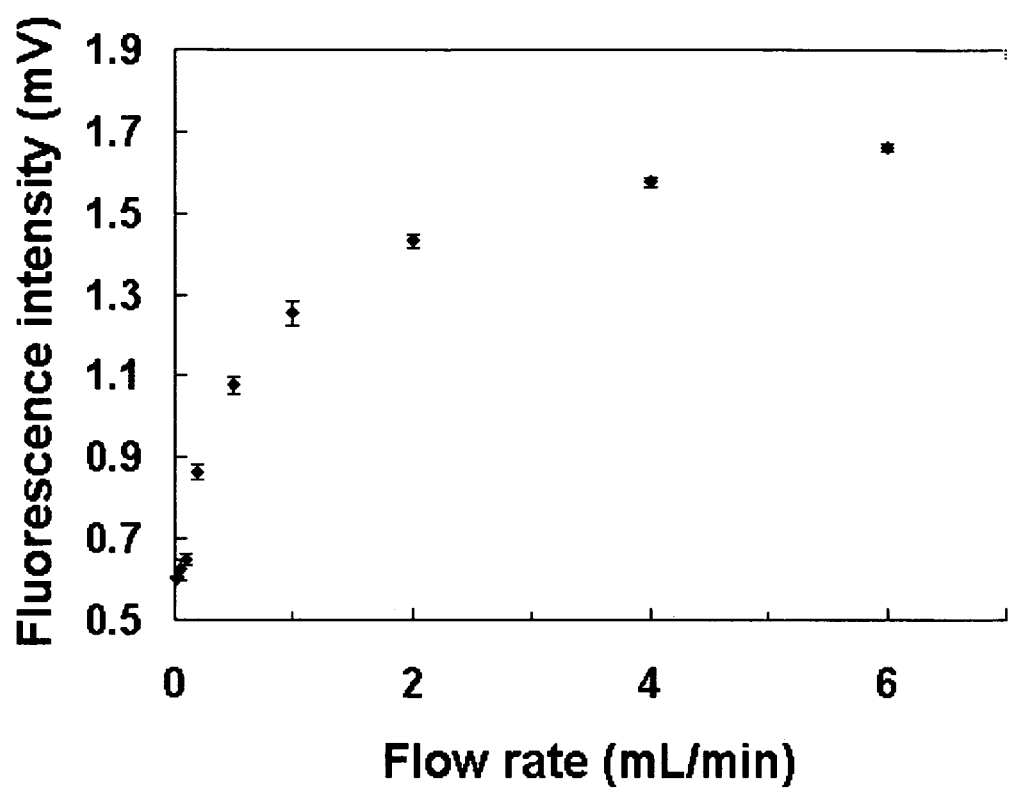
FIG. 10 shows the measured relationship between fluorescent intensity and flow rate for an exemplary LIFPA sensor.

FIG. 10 shows the measured relationship between fluorescent intensity and flow rate for an exemplary LIFPA sensor. The flow rate was measured in the range of 1-6000 μL/min. The LIFPA sensor has linear response at flow rates of 1-100 mL/hr, demonstrating that the technique is sensitive enough to be used as part of a flow control system.

Example 8

Impedance Flow Sensor

An impedance based flow sensor applies an alternating electric field to a target solution flowing through a microcharmel, and changes in the impedance of the solution are measured and correlated with the flow rate. In its simplest form this methodology requires two electrodes at the bottom wall of a channel, applying an AC electric field, and monitoring impedance.

Figure 11:
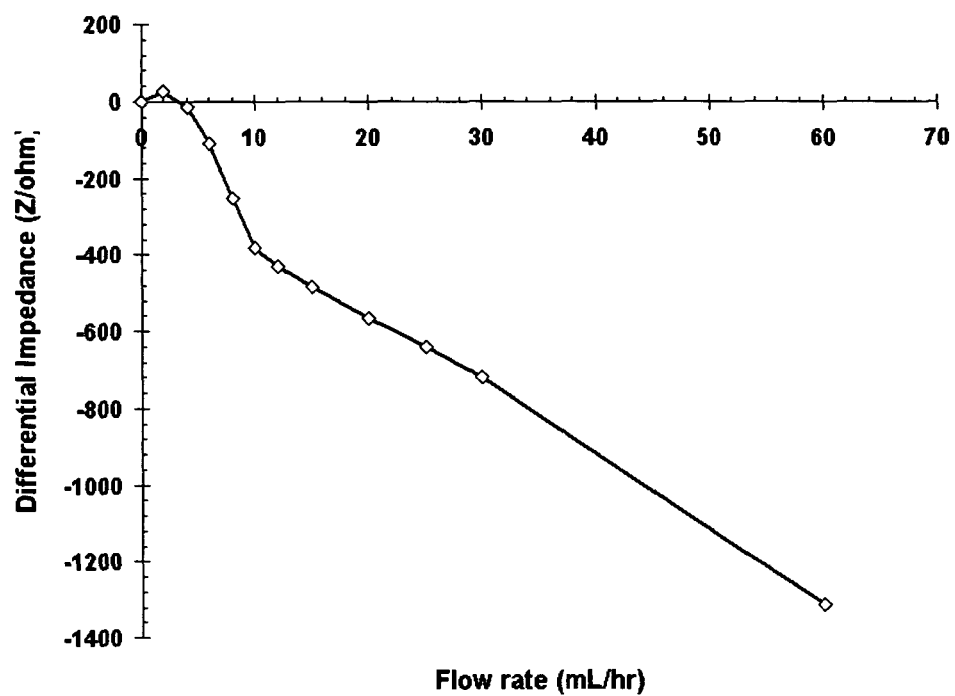
FIG. 11 shows the measured relationship between impedance and flow rate for an exemplary impedance flow sensor.

Flow rate dependent impedance in a microfluidic channel was measured using a simple impedance flow sensor and the results are shown in FIG. 11. The sensor shows a detectable impedance response for flow rates as low as 5 mL/hr and a linear response over flow rates of 10-60 mL/hr.

Figure 12:
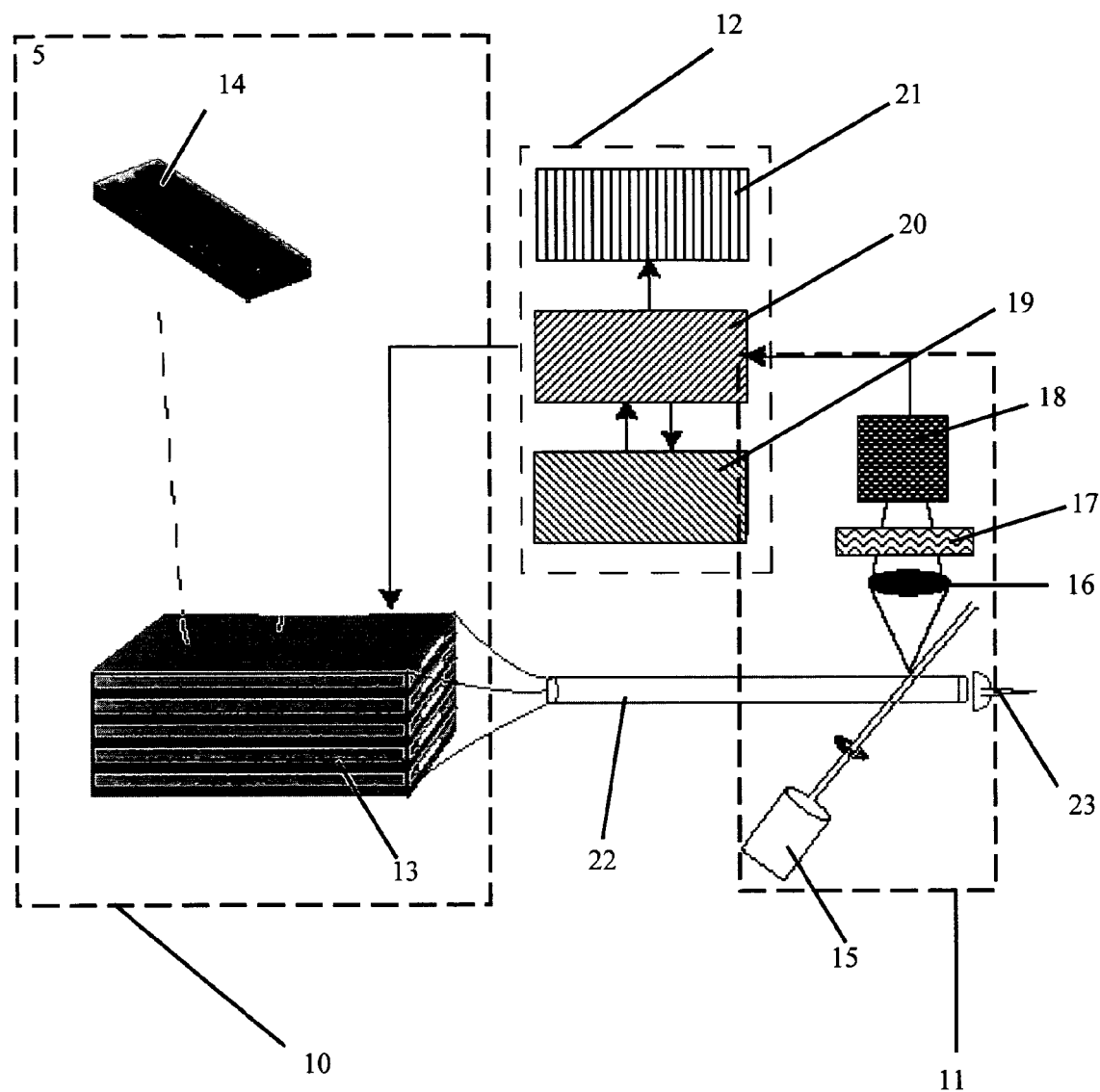
FIG. 12 illustrates design for a miniaturized, self-regulating infusion pump.

An ETF pump, sensor, and controller may be combined, for example, as shown in FIG. 12 to produce a miniaturized infusion pump. The infusion pump comprises a pump 10, flow sensor 11, and controller 12. Pump 10 comprises a stack 13 of ETF micropumps 14. Flow sensor 11, a LIFPA in this case, comprises a laser 15, lens 16, optical filter 17, and photo diode 18. Controller 12 comprises a fluid reservoir (e.g. drug reservoir) 19, a microprocessor 20 that receives flow rate information and controls electrode activation, and a power supply 21.

Pump 10 is connected to a conduit 22 that delivers fluid from the pump to a conduit outlet 23 that is located at a delivery target site in a patient. The micropumps may be arranged in series and/or parallel to produce the desired maximum flow rate and head pressure. Combining 100 micropumps shown in FIG. 8B in parallel, for example would produce a flow rate of 180 mL/min. Combining the same micropumps in series would produce a head pressure of 140 mmHg. An infusion pump have desired maximum flow rate and pressure head specifications can be made by adjusting the numbers of micropumps connected in series with those connected in parallel.

The sensor may be any sensor capable of measuring the rate of fluid flow from the pump to the patient and is preferably a LIFPA or impedance anemometer. The fluid reservoir may contain a drug in fluid form such as an aqueous solution containing an active ingredient or saline solution. The reservoir may comprise compartments containing different drugs for programmed release into a patient. The microprocessor may use flow rate information from the slow sensor to maintain minimum and/or maximum flow rates, provide preprogrammed flow rates, preprogrammed delivery of different drugs or drug combinations from a multi-drug reservoir, and/or provide an emergency cut off in response to abnormal or undesired flow rates.

The patient may be human or other mammal. The term "patients" may also include pets, livestock, and other animals as well as reptiles, amphibians, insects, and plants.

Although particular embodiments of the present invention have been described, it is not intended that such references be construed as limitations upon the scope of this invention except as set forth in the following claims.

The invention claimed is:

1. An electrothermal flow (ETF) pumping device that pumps liquid with electrothermally-induced flow, comprising:
   a pumping chamber having an internal volume with an elongated length along a longitudinal axis defined by a top wall, a bottom wall opposite of the top wall with the internal volume therebetween;
   a fluid inlet fluidically coupled with and located at a first end of the pumping chamber;
   a fluid outlet fluidically coupled with and located at a second end of the pumping chamber, wherein the second end is opposite of the first end with respect to the longitudinal axis;
   one or more first electrode sets of three sequentially arranged parallel elongate electrodes extending laterally across the top wall of the chamber, each first electrode set having a first elongate electrode with a first phase closer to the first end of the chamber and with a third elongate electrode with a third phase closer to the second end of the chamber with a second elongate electrode with a second phase between the first elongate electrode and third elongate electrode, each of the three sequentially arranged parallel elongate electrodes having a different phase and being arranged in a sequence with a phase shift of $2\pi/3$ from the first elongate electrode to the second elongate electrode and to the third elongate electrode,
   one or more second electrode sets of three sequentially arranged parallel elongate electrodes extending laterally across the bottom wall of the chamber, each second electrode set having a first elongate electrode with the first phase closer to the first end of the chamber and with a third elongate electrode with the third phase closer to the second end of the chamber with a second elongate electrode with the second phase between the first elongate electrode and third elongate electrode, each of the three sequentially arranged parallel elongate electrodes of the one or more second electrode sets having a different phase and being arranged in a sequence with a phase shift of 2π/3 from the first elongate electrode to the second elongate electrode and to the third elongate electrode, the first elongate electrode of the one or more first electrode sets being staggered with respect to the first elongate electrode of the one or more second electrode sets, the second elongate electrode of the one or more first electrode sets being staggered with respect to the second elongate electrode of the one or more second electrode sets, the third elongate electrode of the one or more first electrode sets being staggered with respect to the third elongate electrode of the one or more second electrode sets, a first top electrical lead electrically coupled with the first elongate electrodes of the one or more first electrode sets, a second top electrical lead electrically coupled with the second elongate electrodes of the one or more first electrode sets, a third top electrical lead electrically coupled with the third elongate electrodes of the one or more first electrode sets, a first bottom electrical lead electrically coupled with the first elongate electrodes of the one or more second electrode sets, a second bottom electrical lead electrically coupled with the second elongate electrodes of the one or more second electrode sets, a third bottom electrical lead electrically coupled with the third elongate electrodes of the one or more second electrode sets, at least one power supply electrically coupled with the first top electrical lead, second top electrical lead, third top electrical lead, first bottom electrical lead, second bottom electrical lead, and third bottom electrical lead so as to provide the phase shift of 2π/3 from the first elongate electrodes to the second elongate electrodes and to the third elongate electrodes of each of the one or more first electrode sets and the one or more second electrode sets to pump liquid with the electrothermally-induced flow.

2. The ETF pumping device of claim 1, wherein the pumping chamber has one or more of the following dimensions:
a width of 10 mm;
a length of 20 mm; or
a depth of 50 um to 170 um;
wherein the first, second and third electrodes of the one or more first electrode sets and second electrode sets have one or more of the following dimensions:
a width of 10 um to 50 um;
a length of 10 mm; or
a spacing apart from each other of 10 um; or
wherein the ETF pump has a flow rate of 0.758 mL/min to about 1.8 mL/min and a head pressure of 1.4 mmHg to 18.5 mmHg.

3. The ETF pumping device of claim 1, wherein the pumping chamber has the one or more of the following dimensions:
a width of 10 mm;
a length of 15 mm to 4 cm; or
a depth of 100 um;
wherein the first, second and third electrodes of the one or more first electrode sets and second electrode sets have one or more of the following dimensions:

a width of 50 um;
a length of 10 mm; or
a longitudinal spacing apart from each other of 50 um to 70 um; or
wherein the ETF pump has a flow rate of 0.065 mL/min to about 0.078 mL/min and a head pressure of 0.32 mmHg to 0.383 mmHg.

4. The ETF pumping device of claim 1, wherein the pumping chamber has one or more of the following dimensions:
a width of 10 mm;
a length of 20 mm; or
a depth of 170 um;
wherein the first, second and third electrodes of the one or more first electrode sets and second electrode sets have one or more of the following dimensions:
a width of 50 um;
a length of 10 mm; or
a spacing apart from each other of 10 um.

5. The ETF pumping device of claim 1, comprising a fluid in the pumping chamber and the first, second and third electrodes of the one or more first electrode sets and second electrode sets being in contact with the fluid.

6. The ETF pumping device of claim 5, wherein the electrodes include an electrically conducting material that does not react chemically with the fluid.

7. The ETF pumping device of claim 1, wherein the pumping chamber includes an electrically insulating material.

8. The ETF pumping device of claim 7, wherein the electrically insulating material is selected from the group consisting of glass, silicon, or plastic.

9. The ETF pumping device of claim 1, comprising two fluid inlets coupled with and located at the first end of the pumping chamber.

10. A self-regulating electrothermal flow (ETF) drug infusion pumping system, the system comprising:
a plurality of the ETF pumping devices of claim 1;
a fluid reservoir fluidically coupled to each of the fluid inlets of the ETF pumping devices;
a fluid conduit having a conduit inlet fluidically coupled to each of the fluid outlets of the ETF pumping devices and an opposite conduit outlet;
a flow rate sensor fluidically coupled to the conduit outlet; and
a controller having a microprocessor operably coupled to the flow sensor and the power supply, the microprocessor configured to control flow rate of fluid through the fluid conduit.

11. The self-regulating ETF drug infusion pumping system of claim 10, wherein the ETF pumping devices are arranged in series.

12. The self-regulating ETF drug infusion pumping system of claim 10, wherein the ETF pumping devices are arranged in parallel.

13. The self-regulating ETF drug infusion pumping system of claim 10, wherein the flow sensor is configured as a laser-induced fluorescence photobleaching anemometer or a flow induced differential electrochemical impedance spectrometer.

14. The self-regulating ETF drug infusion pumping system of claim 10, comprising:
the fluid reservoir having one or more drug compartments;

the conduit outlet is configured for a placement location for subcutaneous, intradermal, intravenous, intramuscular, intrathecal, intracranial, intraperitoneal, or intraocular drug delivery.

15. The self-regulating ETF drug infusion pumping system of claim 10, wherein at least one pumping chamber has one or more of the following dimensions:
   a width of 10 mm;
   a length of 20 mm; or
   a depth of 50 um to 170 um;
   wherein the first, second and third electrodes of the one or more first electrode sets and second electrode sets have one or more of the following dimensions:
   a width of 10 um to 50 um;
   a length of 10 mm; or
   a spacing apart from each other of 10 um; or
   wherein the ETF pump has a flow rate of 0.758 mL/min to about 1.8 mL/min and a head pressure of 1.4 mmHg to 18.5 mmHg.

16. The self-regulating ETF drug infusion pumping system of claim 10, wherein at least one pumping chamber has the one or more of the following dimensions:
   a width of 10 mm;
   a length of 15 mm to 4 cm; or
   a depth of 100 um;
   wherein the first, second and third electrodes of the one or more first electrode sets and second electrode sets have one or more of the following dimensions:
   a width of 50 um;
   a length of 10 mm; or
   a longitudinal spacing apart from each other of 50 um to 70 um; or
   wherein the ETF pump has a flow rate of 0.065 mL/min to about 0.078 mL/min and a head pressure of 0.32 mmHg to 0.383 mmHg.

17. The self-regulating ETF drug infusion pumping system of claim 10, wherein at least one pumping chamber has one or more of the following dimensions:
   a width of 10 mm;
   a length of 20 mm; or
   a depth of 170 um;
   wherein the first, second and third electrodes of the one or more first electrode sets and second electrode sets have one or more of the following dimensions:
   a width of 50 um;
   a length of 10 mm; or
   a spacing apart from each other of 10 um.

18. The self-regulating ETF drug infusion pumping system of claim 10, comprising a fluid in the pumping chamber and the first, second and third electrodes of the one or more first electrode sets and second electrode sets being in contact with the fluid, wherein the electrodes include an electrically conducting material that does not react chemically with the fluid.

19. The self-regulating ETF drug infusion pumping system of claim 10, wherein the pumping chamber includes an electrically insulating material.

20. The self-regulating ETF drug infusion pumping system of claim 19, wherein the electrically insulating material is selected from the group consisting of glass, silicon, or plastic.

* * * * *